(12) United States Patent
Pettersson et al.

(10) Patent No.: US 7,771,747 B2
(45) Date of Patent: *Aug. 10, 2010

(54) GASTRIC ACID SECRETION INHIBITING COMPOSITION

(75) Inventors: Anders Pettersson, Lilla Edet (SE); Christer Nyström, Uppsala (SE); Yvonne Håkansson, Uppsala (SE)

(73) Assignee: Orexo AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 11/544,750

(22) Filed: Oct. 10, 2006

(65) Prior Publication Data

US 2007/0031497 A1 Feb. 8, 2007

Related U.S. Application Data

(63) Continuation of application No. 10/531,598, filed as application No. PCT/SE03/01598 on Oct. 15, 2003.

(30) Foreign Application Priority Data

Oct. 16, 2002 (SE) ..................................... 0203065

(51) Int. Cl.
*A61K 9/24* (2006.01)
(52) U.S. Cl. ........................ 424/471; 424/464; 424/468; 424/472; 424/474; 424/475; 424/480; 424/490
(58) Field of Classification Search ................. 424/473, 424/472, 407, 470, 469, 468, 476, 474, 490, 424/451, 653
See application file for complete search history.

(56) References Cited

U.S. PATENT DOCUMENTS

| | | | |
|---|---|---|---|
| 4,283,408 A | 8/1981 | Hirata et al. | ................. 424/270 |
| 5,204,118 A | 4/1993 | Goldman et al. | |
| 5,244,670 A | 9/1993 | Upson et al. | ................. 242/439 |
| 5,651,987 A | 7/1997 | Fuisz | |
| 5,840,737 A | 11/1998 | Phillips | ....................... 514/338 |
| 6,013,680 A | 1/2000 | Ogawa et al. | ............... 514/925 |
| 6,077,830 A | 6/2000 | Vertesy et al. | |
| 6,132,768 A | 10/2000 | Sachs et al. | |
| 6,132,771 A | 10/2000 | Depui et al. | |
| 6,183,776 B1 | 2/2001 | Depui et al. | |
| 6,274,173 B1 | 8/2001 | Sachs et al. | |
| 6,316,469 B1 | 11/2001 | Krishnan et al. | |
| 6,489,346 B1 | 12/2002 | Phillips | ....................... 514/338 |
| 6,645,988 B2 | 11/2003 | Phillips | ....................... 514/338 |
| 6,699,885 B2 | 3/2004 | Phillips | ....................... 514/338 |
| 6,852,739 B1 | 2/2005 | Garvey et al. | |
| 6,949,264 B1 | 9/2005 | McGrew et al. | |
| 2004/0171646 A1 | 9/2004 | Phillips | ....................... 514/338 |
| 2005/0054682 A1 | 3/2005 | Phillips | ....................... 514/338 |

FOREIGN PATENT DOCUMENTS

| | | |
|---|---|---|
| DE | 199 25 710 | 12/2000 |
| EP | 0 005 129 | 10/1979 |
| EP | 0 147 726 | 7/1985 |
| EP | 0 166 287 | 1/1986 |
| EP | 0 338 861 | 10/1989 |
| GB | 2 163 747 | 3/1986 |
| GB | 2342292 | 4/2000 |
| JP | 2000-63280 | 2/2000 |
| WO | WO 90/06925 | 6/1990 |
| WO | WO 91/19712 | 6/1991 |
| WO | WO 91/19711 | 12/1991 |
| WO | WO 93/11750 | 6/1993 |
| WO | WO 94/27988 | 12/1994 |
| WO | WO 95/01977 | 1/1995 |
| WO | WO 95/17080 | 6/1995 |
| WO | WO95/22320 | 8/1995 |
| WO | WO 97/25065 | 7/1997 |
| WO | WO 97/25066 | 7/1997 |
| WO | WO 98/40054 | 9/1998 |
| WO | WO 99/04773 | 2/1999 |
| WO | WO 9933448 A1 * | 7/1999 |
| WO | WO00/09092 | 2/2000 |
| WO | WO 00/78284 | 12/2000 |
| WO | PCT/SE02/00757 | 4/2001 |
| WO | WO 02/083132 | 10/2002 |
| WO | WO02/083132 | 10/2002 |

OTHER PUBLICATIONS

H. Hedenstrom, et al., Intragastric pH after oral amdinistration of single dosaes of ranitidine effervescent tablets, omeprazole capsules and famotidine fast dissolving tablets to fasting heathly volunteers, 1997, 11:1137-1141.*

(Continued)

*Primary Examiner*—Michael G Hartley
*Assistant Examiner*—Micah-Paul Young
(74) *Attorney, Agent, or Firm*—Ryan Kromholz & Manion, S.C.

(57) ABSTRACT

An oral pharmaceutical dosage form comprises pharmacologically effective amounts of an acid-susceptible proton pump inhibitor and an H2 receptor antagonist in combination with at least on pharmacologically acceptable excipient which causes a delayed release and/or an extended release of the proton pump inhibitor. The H2 receptor antagonist is included in the dosage form in such a way that it is rapidly released after administration.

This dosage form is suitable for the treatment of conditions associated with an excessive secretion of gastric acid and provides a suitable combination of a rapid onset and a long-lasting duration of the effect.

The invention also relates to a method for manufacturing such a dosage form and to a method for the treatment of conditions associated with the secretion of gastric acid.

21 Claims, 1 Drawing Sheet

OTHER PUBLICATIONS

M. Gschwantler, et al., Famotidine versus omeprazole in combination with clarithromycin and metronidazole for eradication of *Helicobacter pylori*-a randomized, controled trial, 1999, 13:1063-1069.*

H. Hedenstrom, et al., Intragastric pH after oral administration of single dosage of ranitidine effervescent tablets, omeprazole capsule and famotidine fats dissolving tablets to fasting healthy volunteers, 1997, Ailment Pharmacol Ther 11:1137-1141.*

Eriksson, et al., Omeprazole and H2-receptor antagonists in the acute treatment of duodenal ulcer, gastric ulcer and reflux oesophagitis: a meta-analysis, 1995, European Journal of Gastorenterology & Heaptology, 7:467-475.*

Vakil N. et al, Novel methods of using proton pump inbitors, Gastroenterology Clinic of America, vol. 31, 2002, S85-S88.*

Gschwantler et al., "Famotidine versus orneprazole in combination with clarithromycin and metronidazole for eradication of *Helicobacter pylori*—a randomized, controlled trial", Ailment Pharmacol Ther, 13:1063-1069 (1999).

Eriksson et al., "Omeprazole and $H_2$-receptor antagonists in the acute treatment of duodenal ulcer, gastric ulcer and reflux oesophagitis: a meta-analysis", European Journal of Castorenterology & Hepatology, 7(5):467-475 (1995).

Hedenström et al., "Intragastric pH after oral administration of single doses of ranitidine effervescent tablets, omeprazole capsules and famotidine fast-dissolving tablets to fasting healthy volunteers", Ailment Pharmacol Ther, 11:1137-1141 (1997).

Hurlimann et al., "Comparison of acid inhibition by either oral high-dose ranitidine or omeprazole", Ailment Pharmacol Ther, 8:193-201 (1994).

Hunyady et al., "Statistical interpretation of the antisecretory effect of famotidine measured by intragastric pH-metry", Eur. J. Clin. Pharmacol., 50:449-456 (1996).

Hoogerwerf et al., "Agents Used for Control of Gastric Acidity and Treatment of Peptic Ulcers and Gastroesophageal Reflux Disease", Goodman & Gilman's, the Pharmacological Basis of Therapeutics (Tenth Edition) McGraw-Hill, published Sep. 2001, pp. 1005-1020.

DeGraef et al., "Influence of the Stimulation State of the Parietal Cells on the Inhibitory Effect of Omeprazole on Gastric Acid Secretion in Dogs",*Gastroenterology*, Aug. 1986; vol. 91, No. 2, pp. 333-337.

Pharmaceutics the Science of Dosage Form Design, 1$^{st}$ Edition, Ed. M.E. Aulton, Churchill Livingstone, Edinburg 1988, pp. 289-305.

Andersson, T. et al. *Br. J. clin. Pharmac*. 31, 1991, 275-278.

Cheng, D. *Canadian Pharmaceutical Journal* 135, 2002, 27-45.

Hirschowitz, B. et al. *Dig. Dis. Sci*. 40, 1995, 3S-23S.

Hunt, R. et al. *Dig. Dis. Sci*. 40, 1995, 24S-49S.

Katz, P. et al. *Balliere's Best Practice & Research Clinical Gastroenterology* 15, 2001, 371-384.

Nwokolo, C. et al. *Ailment Pharmacol. Ther.* 4, 1990, 29-45.

Peghini P. et al. *Gastroenterology* 115, 1998, 1335-1339.

Richardson, P. et al. *Drugs* 56, 1998, 307-335.

Sachs, G. *Eur. J. Gastroenterol. Hepatol.* 13, 2001, S35-S41.

Sachs, G. et al. *Ann. Rev. Pharmacol. Toxicol.*, 35, 1995, 277-305.

Sachs, G. *Pharmacotherapy* 17, 1997, 22-37.

Shin, J. et al. *Ann. NY Acad. Sci.* 834, 1997, 65-76.

Anderson et al, "Potassium-competitive acid blockade: a new therapeutic strategy in acid-related diseases", Pharmacology 7 Therapeutics, 108:294-307 (2005).

Hunt et al, "Optimizing Acid Suppression for Treatment of Acid-Related Diseases", Digestive Diseases and Sciences, 1995, vol. 40:24S-49S.

Shin et al, "Structural Aspects of the Gastric H,K ATPase", Ann NY Acad Sic 1997 vol. 834:65-76.

Huang et al, "pH, Healing Rate, and Symptom Relief in Patients with GERD", Yale J Biol Med 1999 72:181-194.

Sachs et al, "The Pharmacology of the Gastric Acid Pump: The H+, K+ ATPase", Annu Rev Pharmacol Toxicol 1995 vol. 35:277-305.

Nwokolo et al, "Tolerance during 29 days of conventional dosing with cimetidine, niztidine, famotidine or ranitidine", Aliment Pharmacol Ther 1990, vol. 4:29-46.

Hirschowitz et al, "Pharmacological Aspects of Acid Secretion", Dig Dis Sci 1995, vol. 40:3S-23S.

Sachs, George; "Improving On PPI-Based therapy of GORD" Eur J Gastroentereo Hepatol vol. 13:S35-S41 2001.

Sachs, George, "Proton Pump Inhibitors and Acid-Related Diseases", Pharmacotherapy 1997 vol. 17:22-37.

Richardson et al, "Proton Pump Inhibitors Pharmacology and Rationale for Use in Gastrointestinal Disorders", Drugs 1998 vol. 56:307-335.

Soll, Andrew; "Gastric, Duodenal and Stress Ulcer", Gastrointestinal Disease, Fifth Edition 1993, vol. 1, pp. 600-630.

Federal Register, vol. 39, No. 108—§3331 1-331 11, Tuesday, Jun. 4, 1974.

Fass et al., "Nonerosive Reflux Disease—Current Concepts and Dilemmas", The American Journal of Gastroenterology, vol. 96, No. 2 pp. 303-314, 2001.

Wolfe et al, "Acid Suppressin: Optimizing Therapy for Gastroduodenal Ulcer-Healing, Gastroesophageal Reflux Disease and Stress-related Erosive Syndrome" Gastroenterology 20000; 118:S9-S31, correct date: 2000.

Vakil, N., "Review article: cost-effectiveness of different GERD management strategies" Aliment Pharmacol Ther 20002: 16 (Suppl. 4): 79-82, correct date: 2002.

Soll, Andrew, Peptic-Ulcer and Its Complications: Sleisenger & Fordtran's Gastrointestinal and Liver Disease Pathophysiology/Diagnosis/Management; 6th Edition vol. 1 1998; pp. 620-651.

Related U.S. Appl. No. 10/475,254, filed Dec. 10, 2008, Office Action.

Related U.S. Appl. No. 10/475,254, filed Sep. 3, 2008, Interview Summary (Aug. 26, 2008).

Related U.S. Appl. No. 10/475,254, filed May 30, 2008, Office Action.

Related U.S. Appl. No. 10/475,254, filed Apr. 22, 2008, Interview Summary (Apr. 15, 2008).

Related U.S. Appl. No. 10/475,254, filed Feb. 29, 2008, Office Action.

Related U.S. Appl. No. 10/475,254, filed May 30, 2007, Interview Summary (May 23, 2008).

Related U.S. Appl. No. 10/475,254, filed Mar. 8, 2007, Office Action.

Related U.S. Appl. No. 10/475,254, filed Aug. 8, 2006, Office Action.

Related U.S. Appl. No. 10/475,254, filed Apr. 14, 2006, Office Action.

Curriculum Vitae (CV) of Nimish Vakil, M.D., FACP, FACG (Exhibit 1 to Vakil Declaration), updated Jan. 2009.

Dent, Armstrong, Delany, Moayyedi, Talley, Vakil, "Symptom Evaluation in Reflux Disease: Workshop Background, Processes, Terminology, Recommendations, and Discussion Outputs," *Gut* 2004; 53 (Suppl IV):iv1-iv24) (Attachment 12 to Vakil Declaration).

Vakil et al, "The Montreal Definition and Classification of Gastroesophageal Reflux Disease: A Global Evidence-Based Consensus," *Am J Gastroenterology* 2006: 101:1900-1920 (Attachment 13 to Vakil Declaration).

Flock, Jones, and Vakil, "Approach to Gastroesophageal Reflux Disease in Primary Care," *Can Fam Physician* 2008; 54:701-5) (Attachment 14 to Vakil Declaration).

*American Journal of Gastroenterology*, vol. 96, No. 2, 2001. pp. 303-314, accepted for publication Oc. 6, 2000) (Attachment 2 to Vakil Declaration).

Title 21 U.S.C. § 331.11 (Food and Drugs) (1974) (Attachment 3 to Vakil Declaration).

N. Vakil, "Review Article: Cost-Effectiveness of Different GERD Management Strategies," *Aliment Pharmacol Ther* 2002; 16 (Suppl. 4): 79-82, p. 80) (Attachment 4 to Vakil Declaration).

Vakil, "Novel Methods of Using Proton-Pump Inhibitors," *Gasteroenterol Clin N Am* 31 (2002) S85-88, 87-88) (Attachment 5 to Vakil Declaration).

Vakil et al., "The Effect of Over-the-Counter Rantidine 75 mg on Night-Time Heartburn in Patients With Erosive Oesophagitis on Daily Proton Pump Inhibitor Maintenance Therapy," *Aliment Pharacol Ther* 23 (2006), 649-653 ) (Attachment 11 to Vakil Declaration).

M. Michael Wolfe, M.D. (Professor, Boston University School of Medicine) and George Sachs, M.D. (Professor, UCLA School of Medicine), "Acid Suppression: Optimizing Therapy for Gastroduodenal Ulcer Healing, Gastroesophageal Reflux Disease, and Stress-Related Erosive Syndrome," *Gastroenterology* 2000; 118:S9-S31 (Attachment 6 to Vakil Declaration).

6th Edition of Schlesinger and Fordtran's *Gastrointestinal and Liver Disease (Pathophysiology/Diagnosis/Management)* (1998) (Attachment 7 to Vakil Declaration).

5th Edition of Schlesinger and Fordtran's *Gastrointestinal and Liver Disease (Pathophysiology/Diagnosis/Management)* (1993) (on pp. 626-627) (Attachment 8 to Vakil Declaration).

United States Patent 5,229,137 (issued Jul. 20, 1993) (Attachment 9 to Vakil Declaration.

Fändriks, Lönroth, Pettersson, *Scandinavian Journal of Gasteroenterology* (*Scandinavian Journal of Gasteroenterology*, "Can Famotidine and Omeprazole be Combined on a Once-Daily Basis?" 2007; 42: 689-694) (Attachment 10 to Vakil Declaration.

Related U.S. Appl. No. 11/822,502, filed Feb. 20, 2009, Office Action.

Related U.S. Appl. No. 11/822,502, filed Jun. 04, 2008, Office Action.

Office Action mailed Sep. 29, 2009 (U.S. Appl. No. 10/475,254).

Interview Summary, U.S. Appl. No. 10/475,254, Jan. 7, 2010.

Amendment F with Summary of Interview, U.S. Appl. No. 10/475,254, Jan. 19, 2010.

\* cited by examiner

GASTRIC ACID SECRETION INHIBITING COMPOSITION

FIELD OF THE INVENTION

The present invention relates to a gastric acid secretion inhibiting composition, to a method for its manufacture and to its use in treating conditions which are related to the secretion of gastric acid.

BACKGROUND OF THE INVENTION

During the latest decades, much progression has been made in the suppression of acid secretion, an integral part of the treatment of dyspeptic disorders such as gastro-oesophageal reflux disease (GORD), duodenal and gastric ulcers and non-ulcer dyspepsia. Although the pathophysiology of these disorders is not identical, the inhibition of gastric acid secretion is pivotal to healing organic lesions, alleviating symptoms of discomfort and improving the quality of life. Moreover, acid-related damage may underlie the progression to cancers and other late complications of these conditions. Inhibition of acid secretion is also a cornerstone in the treatment regimens aiming for eradication of *Helicobacter pylori* infection.

Dyspepsia (acid dyspepsia) is a common disorder. Heartburn is a symptom of dyspepsia. It is estimated that 44% of Americans have heartburn at least once monthly but that only about 25% of them are seeing the doctor because of their dyspepsia problem. Symptoms associated with dyspepsia are for instance upper abdominal pain/discomfort and heartburn, indigestion, "sour" stomach, and gastro-esophageal reflux.

Dyspepsia is a multi-factorial disease and may be associated with organic pathology such as duodenal ulcer, gastric ulcer, esophagitis, Barrett's esophagus or gastro-duodenal inflammation (e.g., *Helicobacter pylori* infection). Dyspepsia also includes conditions where no organic pathology can be found, e.g., non-ulcer dyspepsia (NUD) or functional dyspepsia.

Dyspepsia can be controlled by administration of medicines that raise the pH in the stomach. Therapeutic agents effective in the treatment of dyspepsia include gastric acid suppressing agents, such as histamine H2 receptor antagonists (in the following called H2 receptor antagonists), acid susceptible proton pump inhibitors, antacids/alginates, anticholinergics and prokinetic agents. They can be distinguished by their mechanism of action, safety profile, and pharmacokinetics. The stomach pathogen *Helicobacter pylori* has been associated with dyspepsia, gastro-duodenal ulcer disease and stomach cancer. The treatment of *H. pylori* infection usually comprises the administration of a combination of acid secretion suppressing agents and one or two antibiotic agents.

The therapeutic effect on dyspepsia-related discomfort and organic lesions when inhibiting acid production by administration of acid secretion-inhibiting drugs is related to the degree of acid inhibition as well as to the onset and duration of action of the particular drug. The majority of patients who have symptomatic acid reflux disease have a normal esophageal mucosa or only a mild degree of oesophagitis. Treatment to relieve symptoms as they occur may be the best way to manage these patients, to whom the speed of symptom relief is of primary importance.

Antacid agents, that is, acid-neutralizing agents, and alginates are the first therapeutic choice in the treatment of mild heartburn. They have a extremely short duration of action but are seen as inexpensive and safe. Antacid agents work locally through a neutralization of gastric acid. Alginates provide some mechanical protection against reflux of gastric acid into the esophagus. The main advantages of antacid agents and alginates are that they provide fast relief of symptoms. The main disadvantage of antacid agents and alginates is their extremely short duration of action, and dosing has to be repeated frequently to keep the patients free of symptoms, further that antacids often do not provide symptom resolution, i.e. complete relief of symptoms. Moreover, these agents are not at all useful in the treatment of acid induced organic lesions, GORD or *Helicobacter pylori* infection.

Several classes of compounds are known which affect the secretion of gastric acid. Among them, acid susceptible proton pump inhibitors, such as the substituted benzimidazoles omeprazole, lanzoprazole, rabeprazole and pantoprazole and histamine H2 receptor antagonists, such as cimetidine, ranitidine and famotidine are the most prominent ones. H2 receptor and acid susceptible proton pump inhibitors are widely prescribed for reducing gastric acid secretion systemically.

The design of acid suppression therapy requires a detailed understanding of the mechanisms behind the secretion of hydrogen ions, namely the parietal cell and hydrogen-potassium adenosine triphosphate ($H^+,K^+$-ATPase) so that these mechanisms can be effectively targeted with pharmacological intervention. Three key factors have been identified in order to achieve an effective pharmacological treatment of acid related disorders (*Dig Dis Sci* 1995 vol 40: 24S-49S. Optimizing acid suppression for treatment of acid-related diseases.):

1) Time to onset of action, i.e. the inhibition of acid secretion should occur as rapidly as possible.

2) Degree of acid inhibition, i.e. the intragastric pH should be kept well above 4.

3) Duration of action, i.e. the inhibition of acid secretion should remain virtually complete during 24 hours on the first dose and remain complete during the course of treatment.

All of these factors must be considered when deciding how to optimize said suppressive therapy. However, several aspects of the parietal cell physiology and the pharmacology/biochemistry of existing pharmaceuticals have to date prevented the achievement of this goal.

Central to the acid secretory mechanism are the parietal cells of the stomach. These cells secrete hydrogen ions into the gastric lumen under the control of neurocrine, paracrine and endocrine pathways. One of the major paracrine factors is histamine released by the enterochromaffine-like (ECL) cells. The histamine released from the ECL cells stimulates parietal cells to acid secretion via histamin-2(H2) receptors located on the cell surface. Engagement of these receptors results in cyclic adenosine-3,5-monophosphate (cAMP) elevation and cAMP binding to the regulatory subunit. A variety of proteins will be phosphorylated, all of which will be relevant to activation of secretion. The molecular dissection of this intracellular pathway is far from complete, however, the action of cAMP includes translocation of $H^+,K^+$-ATPase into the secretory canaliculus and activation of the KCL transporters, i.e. put the parietal cell into a secretory state.

The first attempts of decreasing acid secretion targeted the paracrine pathway, namely the histamine H2 receptor activation-induced stimulation of acid secretion. Accordingly, the first class of acid inhibitors was the H2 receptor antagonists (H2 blockers), including compounds such as cimetidine, ranitidine, famotidine and nizatidine. Their mode of action is to antagonize the effects of histamine, i.e. to inhibit the recruitment of proton pumps to the secretory canaliculus and reduce the activity of KCL transport. This will put the parietal cells into a non-secretory state and thereby reduce the output of hydrogen ions (*Dig Dis Sci* 1995, vol 40:3S-23S. Pharmacological aspects of acid secretion).

However, phenomena of acid rebound and tolerance are major drawbacks to the use of these drugs in treating acid related diseases. There is an approximately 50% loss in acid reduction capacity during repeated dosing, which severely restricts the use of this class of drug in the treatment of, for example, GORD (*Aliment Pharmacol Ther* 1990, vol 4: 29-46. Tolerance during 29 days of conventional dosing with cimetidine, nizatidine, famotidine or ranitidine). Moreover, these agents are not at all useful in the treatment of *Helicobacter pylori* infection, a treatment dependent on an effective and sustained reduction of acid secretion.

Current treatment of acid related disorders is focused on a more direct target, the $H^+,K^+$-ATPase ("proton pump") of the active parietal cell. These cells constitute the final acid sources—the acid secretory canaliculus and the acid pump itself. Therefore, drugs designed to inhibit acid secretion at this level show a greater efficacy and specificity. Because proton pump inhibitors (PPIs) act at a step downstream of the parietal cell stimulus, tolerance does not occur with the use of these compounds, in contrast to the H2 receptor antagonists. Moreover, these drugs hit the final target to which all other pathways converge, the $H^+,K^+$APPase in the acid space or canaliculus of the stimulated parietal cell.

Individual PPIs are similar with respect to their general structure, which consists of a substituted pyridylmethylsulfinyl benzimidazole. PKa values for these compounds vary from 4.0 to 5.0. All PPIs share the same pharmacological mechanism that is essentially the same: their pKa restricts accumulation of the compound to acid spaces, such as that in the parietal cell. PPI accumulation in the canaliculus of the parietal cell is followed by an acid-dependent activation step whereby the PPI is converted to sulphenic acid or sulphenamides. Formation of these reactive intermediates allows for binding to cysteine residues within the exposed luminal surface of the $H^+,K^+$-ATPase. The enzyme is functionally inactivated via the production of covalent disulphide bonds. The inhibition of $H^+,K^+$-ATPase by PPIs thus results in a relatively stable inhibition of the enzyme, as de novo synthesis of the enzyme is required to reverse the inhibition. These mechanisms of action is described in *Dig Dis Sci* 1995, vol 40:3S-23S. Pharmacological aspects of acid secretion.

One of the fundamental characteristics of the PPIs is that they are only functional in active parietal cells, i.e. the cells have to be in a secretory state. The reason for this is three-fold. Firstly, in most parietal cells, the acid space (canaliculus) has a pH of about 1.0. At this pH, the pKa values of PPIs allow them to accumulate in the parietal cell 1000- to 10,000-fold. However, at higher pH, for example 3, this accumulation decreases by two orders of magnitude, i.e. to 10- to 100-fold. Thus, the weak base characteristics of the PPIs allow them to accumulate only when acid is being formed by the parietal cell. This becomes important when administering PPIs during conditions when the parietal cell is put into a non-secretory state. Secondly, the conversion of PPI to sulphenic acid or sulphenamide is an acid-dependent process. Thirdly, the $H^+,K^+$-ATPase has to be activated, i.e. the enzyme has to be inserted into the membrane of the secretory canaliculus, where its cysteine residues can be reached by the sulphenamides (*Pharmacotherapy* 1997 vol 17:22-37. Proton pump inhibitors and acid related diseases; *Drugs* 1998 vol 56:307-335. Proton pump inhibitors: pharmacology and rationale for use in gastrointestinal disorders; *Ann NY Acad Sci* 1997 vol 834:65-76 Structural aspects of the gastric $H^+$, $K^+$-ATPase; *Annu Rev Pharmacol Toxicol* 1995 vol 35:277-305. The pharmacology of the gastric acid pump).

These characteristics of the pharmacology/biochemistry of the PPIs will profoundly affect the pharmacodynamics of this class of compounds. On one hand, these drugs require an active enzyme for inhibition and some pumps are not active while the drug is present in the blood. On the other hand, the PPIs exhibit a relatively short plasma half-life of 60 minutes, and new pumps are synthesized at a rate of 25% per 24 hours.

These facts point to the therapeutic dilemma of PPIs at present. As the compounds are accumulated and converted in the acidic space of the parietal cell, only those pumps which are secreting acid will be inhibited. Since the cell has a reserve of inactive pumps and is in the process of synthesizing new pumps, many pumps destined to be active within the next 24 hours will not be inhibited by the first dose. However, the following day, when PPI is given again, new pumps have been recruited and can be inhibited, and the pumps inhibited 24 hours previously have not been replenished entirely. Therefore, the response to PPIs is cumulative, reaching a steady state and therapeutic acid inhibition first after at least three consecutive days of treatment.

Thus, the current concept regarding PPIs mechanisms of action is the need for active pumps to mediate their effects. In the resting state, parietal cells produce no acid and the pumps are inactive. The inhibition of acid production by PPIs occurs when these pumps are in the active state, via accumulation in the parietal cell, such that subsequent activation of the drug results in an inhibition of the pump (*Eur J of Gastroentereol Hepatol* 2001 vol 13:S35-S41. Improving on PPI-based therapy of GORD)

In summary, neither class of anti-secretory drugs available today attain the goal for acid control stated above, i.e. of a rapid onset of action, potent inhibition of acid secretion and a sustained duration of action during the course of treatment. This goal is of the utmost importance for the clinical outcome of treatment, as the therapeutic effect is related to the onset, degree and duration of action, i.e. how quickly, how much and for how long the pH is raised in the stomach.

Various combinations of antacid and/or mucosa-protecting agents with agents that reduce acid secretion have been disclosed to be useful in treating dyspepsia.

WO 95/01708 describes a composition for use in the treatment of for instance heartburn comprising an H2 receptor antagonist, such as famotidine, and an alginate and optionally simethicone (an activated polysiloxane).

EP 338861 A describes a solid pharmaceutical preparation consisting of an antacid and excipients which is proposed to be used in combination with an acid-susceptible proton pump inhibitor or any other substance inhibiting gastric acid secretion. There is no suggestion to combine these substances in a fixed unit dosage form.

U.S. Pat. No. 5,244,670 A describes an ingestible pharmaceutical composition comprising a substance selected from the group consisting of antacid agents, acid secretion-prevention agents, bismuth-containing agents and their mixtures, and 3-(1-menthoxy)-propane-1,2-diol which is present to provide a cooling sensation to the throat.

WO 97/25066 discloses a pharmaceutical formulation comprising a combination of an acid-susceptible proton pump inhibitor or an H2 receptor antagonist and one or more antacid agents or alginates.

Neither acid-susceptible proton pump inhibitors nor H2 receptor antagonists, alone or in combination with antacids and/or alginates, provide fully satisfactory quick and lasting relief to patients, to whom the speed of symptom relief is of primary importance but who also desire to be free of symptoms for a longer period of time. Thus, none of the solid pharmaceutical preparations for per-oral administration reported to date, satisfies the basic requirements; rapid onset of acid secretion inhibition, potent reduction of acid secretion and a sustained inhibition of acid secretion.

Furthermore, the use of proton pump inhibitors has a serious shortcoming regarding chemical stability:

The substances are extremely acid-labile, which has made special formulations necessary. Normally, the substances are protected in vivo by the application of a gastric acid-resistant coating (enteric coating) over the active substance. As such coatings in themselves are acidic (release hydrogen ions), it has been found that it is also necessary to provide some sort of protection in vitro, i.e. when the product is stored.

This protection in vitro may be arranged such as is described in U.S. Pat. No. 6,183,776 B1 (Depui et al.), where an alkaline-reacting substance is added together with the proton pump inhibitor, and a supplementary protective coating (sub-coat) is applied just under the gastric acid-resistant coating.

Another approach is disclosed in WO 00/78284 (U.S. Pat. No. 5,225,202), where the gastric acid-resistant coating is neutralized such that it shows no acid reaction during storage. After swallowing, the hydrogen ions present in the stomach will acidify the coating and thus recreate the acid-protecting properties of the coating in situ.

It has now been found that both the problem regarding rapid and long lasting relief of symptoms as well as the chemical instability problem of acid susceptible proton pump inhibitors may be solved by the present invention.

OBJECTS OF THE INVENTION

It is an object of the invention to provide a medicine which provides quick and lasting relief to a patient suffering from conditions related to gastric acid secretion.

It is another object of the invention to provide a method for treating a patient suffering from conditions related to gastric acid secretion which provides quick and lasting relief.

Further objects of the invention will be evident from the following short description of the invention, a preferred embodiment thereof, and the appended claims.

SUMMARY OF THE INVENTION

The present invention relates to a solid pharmaceutical dosage form for oral administration, which is characterized in that it comprises a H2 receptor antagonist formulated for a rapid release and a PPI which is formulated for an extended release. In the present dosage form, the rapidly released H2 receptor antagonist will be rapidly absorbed and inhibit acid secretion by the mechanisms described above. The PPI formulated for delayed and/or extended release will maintain a maximal acid suppression already after the first dose and maintain a maximal acid suppression during the course of treatment.

Acid-susceptible proton pump inhibitors are acid-activated prodrugs that covalently inhibit the gastric H+,K+-ATPase, the proton-transporting enzyme involved in the production of hydrochloric acid in the stomach. The action of gastric H+,K+-ATPase represents the final step in the sequence of events resulting in secretion of hydrochloric acid by the parietal cell. Thus inhibition of this enzyme is the most effective and specific means of controlling acid secretion regardless of the nature of the stimulus to secretion. As would be expected with such a mechanism of action, proton pump inhibitors such as omeprazole has been shown to inhibit both basal and stimulated acid secretion. Omeprazole is a weak base which accumulates in the acidic milieu of the secretory membrane of the parietal cell where it undergoes rearrangement in acid to its active sulphenamide form which subsequently reacts with sulfhydryl groups of the acid pump.

In gastric mucosa, the acid-susceptible proton pump is situated in the apical membrane and in the tubovesicles bordering the secretory canaliculus of the parietal cell. Thus, after a single dose, omeprazole rapidly accumulates in the acidic compartment of the secretory membrane where its active sulphenamide form irreversible binds to the H+,K+-ATPase. The H+,K+-ATPase situated in the tubovesicles will however not be exposed for activated omeprazole. A major portion of synthesized H+,K+-ATPase will thus escape blockade after a single omeprazole dose. This may explain why the maximal acid-inhibitory effect of omeprazole is reached only after about five days of treatment.

H2 receptor antagonists competitively inhibit the action of histamine on all H2 receptors, mainly on the surface of the parietal cells. At therapeutic doses, these agents are capable not only of decreasing both basal and nocturnal acid secretion, but also secretion stimulated by food, histamine, insulin and pentagastrin. A single dose of an H2 receptor antagonist results in maximal acid inhibitory effect already within 2 hours after intake. Furthermore, the acid inhibitory effect obtained with high doses of an H2 receptor antagonist is built up rapidly but has a tendency to fade substantially during the following 2-7 days, while the acid inhibitory effect of omeprazole gradually is built up during the same period of time.

The present invention is based on the unexpected finding that an almost complete inhibition of acid secretion is achieved by the first dose of an acid susceptible proton pump inhibitor administered as an extended release formulation. Furthermore, as only activated proton pumps secreting acid during the time PPI is present in the plasma is expected to be inhibited, it was surprisingly found that a sustained inhibition of acid secretion could be achieved while the parietal cells is put into a non-secretory state by means of the rapidly released H2 receptor antagonist.

Thus, according to the invention, there is provided an oral pharmaceutical dosage form comprising pharmacologically effective amounts of an acid-susceptible proton pump inhibitor or a salt thereof, and an H2 receptor antagonist or a salt thereof, and a pharmaceutically acceptable excipients resulting in delayed and/or extended release of the proton pump inhibitor. The terms "proton pump inhibitor" and "H2 receptor antagonist" include their isomers, such as enantiomers of proton pump inhibitors, as well as pharmaceutically acceptable salts of such isomers.

The invention is especially suitable for "on demand" treatment of gastro-esophageal reflux complaints e.g. heartburn, where potent acid reduction is needed for a shorter period of time and where a rapid onset of action is most important and a maximal acid reduction is to prefer. The maximal acid inhibitory effect would be able to be maintained during a 7 days period by the elimination of the "fade-off" phenomenon seen after H2-blocker given alone. This will be important in order to reduce the time for the treatment of stomach ulcers, acid-related lesions in the esophagus and *Helicobacter pylori* eradication.

To overcome the previously mentioned problems associated with the proton pump inhibitors, the invention comprises three parts:

1) By formulating the proton pump inhibitor into a composition which releases active substance with a delayed effect (delayed release) and/or with a prolonged effect (extended release), a composition is obtained which acts completely opposite to what has been desired up to now regarding a rapid onset of the effect. However, a new type of protection for these acid-labile pharmaceutical substances is provided.

This type of release-controlled composition is well-known to those skilled in the art and has a number of different designations.

In the present specification, the expression "extended release" is used as a synonym to "prolonged release" and "sustained release". Irrespective of which expression is used, the common function is that the release of the active substance is retarded and extended over a longer time. This is normally obtained by either providing a core of active substance with a coating or membrane of suitable auxiliary agents which control the release, or by incorporating the active substance in a matrix of suitable auxiliary agents.

The expression "delayed release" is used in the present specification to describe compositions which do not release active substance immediately. The start of the release is thus displaced to the small intestine or large intestine. This type of composition is normally obtained by providing a core of active substance with a coating or membrane which is changed during the transport in the gastro-intestinal tract by the changes in pH encountered by the composition, or by a change in the coating as a function of the time when the composition is in contact with body fluids. The present type of composition is not to be confused with gastric acid-resistant compositions ("non-enteric release"), which are only intended to protect the composition from hydrogen ions or, alternatively, to protect the patient from a deleterious effect of the medical compound on the stomach.

The expressions "controlled release" and "modified release" may also be used to describe this part of the invention, but they constitute more collective designations which do not specifically describe the present type of release mechanisms.

All these types of designations, principles for formulation and suitable auxiliary agents are well-known to those skilled in the art, and reference is here made to the manual "Pharmaceutics. The Science of Dosage Form Design", 1$^{st}$ edition; Ed. M. E. Aulton, Churchill Livingstone, Edinburgh 1988, which is hereby incorporated by reference. Reference is especially made to pages 289-305.

It is clear that the basic composition hereby provided may be combined with further additions of auxiliary agents. Thus, for example, the proton pump inhibitor may be blended with an alkaline reacting substance to neutralize the small amount of hydrogen ions which may pass through the membrane or matrix structures during the passage through the stomach. This measure is not strictly necessary, but leads to a more perfect composition. In the same manner, a gastric acid-resistant coating may be provided on the exterior side of the membrane or matrix part of the composition. In a further embodiment, these two formulation measures may be used at the same time.

2) The problem of a too slow onset of the increase in pH is not obviously solved by further retarding or time-expanding the release. However, it has now turned out that it is possible to administer an H2 receptor antagonist having a rapid onset of effect (obtained through a rapid release), without compromise the onset of action of the subsequently released acid susceptible proton pump inhibitor. This was unexpected since an important feature of PPIs is the need for active pumps to mediate their effects. During influence of an H2 receptor antagonist, the parietal cells are put into a resting state. In the resting state, parietal cells produce no acid and the pumps are inactive. The inhibition of acid production by PPIs occurs only when these pumps are in the active state, via accumulation in the parietal cells, such that subsequent activation of the drug results in an inhibition of the pump. Thus, the present invention provides a novel pharmacological composition utilizing the rapid inhibition of acid secretion from a histamine 2 receptor antagonist without offsetting the effect of the concomitantly administered PPI.

3) From the current knowledge of PPI mode of action and the biochemistry of $H^+$, $K^+$-ATPase, it is not obvious how to achieve maximal inhibition of acid secretion with the first dose of a PPI (wide supra).

However, it has now turned out that expanding the time during which PPI is released results in an unexpected efficient first dose inhibition of acid secretion. By extend the time for PPI present in the blood, newly synthesized pumps will be continuously inactivated. This was unexpected, as following the initial inhibition of the pump, the pH in the secretory space would rise and the drug will depronate and diffuse back out of the canaliculus. Furthermore, the second clearly essential step in the the PPIs action, the acid-catalysed conversion into the active sulphenamide, would not take place.

The combination described here may be obtained in two ways. Firstly, a separate dose having a delayed/extended release of the proton pump inhibitor may be administered concurrently with a separate dose of the H2 receptor antagonist. Alternatively, these two substances having different release profiles may be combined into the same preparation. A number of examples will illustrate how this is suitably arranged.

Thus, the present invention provides a sustained acid suppression already after the first dose. This cannot be attained by the products proposed by the prior art:

H2 blockers are only active during the first 6-8 hours.

H2 blockers+antacids give a rapid onset, but are only active for 6-8 hours

PPIs give no action at all after the first dose.

PPIs+antacids are active for about one hour through the antacid effect.

PPI enantiomer will not reach its full potential after the first dose.

PPI slow release alone will give an effect first after 5-6 hours

Thus, the present invention provides an important improvement over the formulations of the prior art. This improved effect is considered to be due to the unexpected clinical/physiological effect attained through the unique preparation of the invention, i.e. the delayed/extended effect of the PPI in combination with the rapid release of the H2 blocker.

Some patent publications are known which disclose combinations of a proton pump inhibitor and compositions for delayed release, and reference may here be made to U.S. Pat. No. 6,132,768, U.S. Pat. No. 6,274,173 B1 and DE 199 25 710 A1. These references are directed to increasing the stability of proton pump inhibitors against degradation and discoloration caused by hydrogen ions. However, they do not teach anything about any combination of a proton pump inhibitor and an H2 receptor antagonist and the unexpected advantages attained thereby.

Furthermore, a gastric acid secretion inhibiting composition is known from the international patent application PCT/SE02/00757. This composition comprises a combination of an acid-susceptible proton pump inhibitor and an H2 receptor antagonist, but no mention is made of the excipient system of the present invention and its unexpected advantages.

According to the invention, there is provided an oral dosage form comprising an H2 receptor antagonist in an amount effective to reduce the acidity in the stomach after administration and an acid-susceptible proton pump inhibitor in an amount effective to sustain the low acidity effected by the H2 receptor antagonist over an extended period of time. It is preferred for the pharmacologically effective amounts to be amounts capable of raising gastric pH to above 3 within 2 hours from administration and to keep it above 3 for at least 4 hours, preferably for at least 8 hours. It is more preferred for said pharmacologically effective amounts to be amounts capable of raising gastric pH to above 4 within two hours after administration and to keep it above 4 for at least 8 hours, more preferred for at least 16 hours.

According to a first preferred aspect of the invention the H2 receptor antagonist is provided in an amount which is capable of providing at least 80% of maximal reduction, more preferred at least 95% of maximal reduction, of the acidity in the stomach within about two hours. "Maximal reduction" is the reduction of acidity which can be maximally obtained by administering an H2 receptor antagonist alone in therapeutically accepted amounts, that is, in amounts in which such drugs are administered in the art. The term "H2 receptor antagonist(s)" as used herein includes all agents that substantially inhibit or block the secretion of gastric acid by binding to histamine type 2 receptors in the stomach. At therapeutic doses such H2 receptor antagonists are capable not only of decreasing basal and nocturnal acid secretion, but also secretion stimulated by food, histamine, insulin and pentagastrin. Exemplary H2 receptor antagonists according to the invention are cimetidine, ranitidine, nizatidine and famotidine which are normally used in the form of their pharmacologically acceptable salts, in particular hydrochlorides. The dosage form of the invention preferably comprises from 1 mg to 800 mg of H2 receptor antagonist or salt thereof, more preferred from 5 mg to 400 mg.

According to a second preferred aspect of the invention the acid-susceptible proton inhibitor is provided in an amount which is capable of maintaining the low acidity effected by the histamine H2 antagonist over at least 6 hours. Acid-susceptible proton pump inhibitors are rapidly taking market share from H2 receptor antagonists. The term "acid-susceptible proton pump inhibitor(s)", as used herein, comprises benzimidazole derivatives having substantial H+,K+-ATPase inhibiting activity, in particular omeprazole, pantoprazole, lanzoprazole, rabeprazole, pariprazole, leminoprazole and their pharmaceutically acceptable salts and enantiomers and salts of enantiomers, but include also the other compounds disclosed on pages 7-11 of WO 97/25066 which are hereby incorporated by reference as well as those disclosed in EP 005 129 A1, EP 174 726 A1, EP 166 287 A1, GB 2 163 747, WO 90/06925, WO91/19711, WO91/19712, WO94/27988, WO95/01977.

Thus the dosage form of the invention comprises preferably from 1 mg to 100 mg, more preferred from 5 mg to 50 mg, per single dose of an acid-susceptible proton pump inhibitor or a salt thereof. The acid-susceptible proton pump inhibitor or salt thereof is separated from the H2 receptor antagonist by the formulation principle, where only the proton pump inhibitor is coated by the membrane or incorporated in a matrix for the purpose of delayed and/or extended release.

According to a third preferred aspect of the invention the H2 receptor antagonist formulated for rapid release and the acid-susceptible proton pump inhibitor formulated for delayed and/or extended release need not to be comprised by the same pharmaceutical composition but may be administered separately but within a narrow time interval, such as a time interval of one hour, in particular a time interval of 30 min, most preferred a time interval of 10 min. Thus is disclosed a corresponding dose regimen for separate but joint administration of an acid-susceptible proton pump inhibitor and an H2 receptor antagonist to treat a condition related to gastric acid secretion.

The oral dosage form of the invention thus comprises an acid-susceptible proton pump inhibitor formulated for delayed and/or extended release, an H2 receptor antagonist formulated for rapid release and, optionally, a gastric acid-suppressing agent and/or an alginate. Preferably, the dosage form of the invention comprises from 100 mg to 1000 mg of antacid agent and/or alginate. The antacid agent of the invention comprises one or several of aluminum hydroxide, calcium carbonate, magnesium carbonate, basic magnesium carbonate, magnesium hydroxide, magnesium oxide and sodium hydrogen carbonate.

Due to the fact that acid-susceptible proton pump inhibitors are generally sensitive to acid (acid-susceptible proton pump inhibitors) they need to be administered in a form which protects them from degradation in the stomach to make them pass into the small intestine where they are absorbed. In this new invention, this is largely solved by the use of excipients for delayed and/or extended release which offers protection, without the known disadvantage of enteric coating layers (i.e. liberation of hydrogen ions, that will increase the degradation rate of the proton pump inhibitors). H2 receptor antagonists, on the other hand, can be administered without such protection. According to a further preferred aspect of the invention, compositions can be adapted to suit the purpose of the present invention are among those disclosed in WO 97/25066.

The oral dosage forms of WO 97/25066 comprise an acid-susceptible proton pump inhibitor in an amount similar or identical to that used in the composition of the present invention, and one or several antacid agents and/or alginate(s). The adaptation of the compositions of WO 97/25066 essentially consists firstly, in adding the membrane—or matrix system to the part of the formulation that contains the proton pump inhibitor and secondly, in substituting a pharmacologically effective amount of an H2 receptor antagonist for a portion of or the entire amount of the antacid agent(s) and/or alginate.

According to the invention, there is provided an oral, multiple-unit tableted dosage form comprising an acid-susceptible proton pump inhibitor in individually delayed/extended release coated units optionally coated with an enteric coating layer in combination with an H2 receptor antagonist in the form of a powder or granules compressed into a tablet. The enteric coating layer(s) covering the individual units of the acid-susceptible proton pump inhibitor has properties such that the compression of the units into a tablet does not significantly affect the acid resistance of the individually coated units. Furthermore, the multiple unit tableted dosage form provides a good stability to the active substances during long-term storage.

According to the invention, there is also provided a multiple-unit tableted dosage form, which is divisible and easy to handle. Such a multiple-unit tableted dosage form comprises delayed/extended release coated pellets of an acid-susceptible proton pump inhibitor optionally coated with an enteric coating layer compacted with a powdery H2 receptor antagonist. This dosage form may also contain effervescent components for making it disintegrate rapidly when put into water. The pH of the aqueous phase must then be made slightly acidic to prevent dissolution of any present enteric layer. This dosage form can be given to patients with swallowing disorders and in pediatrics. Such a suspension of dispersed units/ pellets of appropriate size can be used for oral administration and also for feeding through a naso-gastric tube.

According to the invention, there is also provided a tablet preparation comprising an acid-susceptible proton pump inhibitor in admixture with tablet excipients forming a tablet core which is coated with excipients for delayed and/or extended release, and a separate layer surrounding the tablet core. The surrounding layer comprises an H2 receptor antagonist in admixture with a pharmaceutical excipient. Optionally a separating layer is applied on the tablet core before the core is covered with the coating. A further option is than to also apply, on top of the other coats, an enteric coating layer. Alternatively, the prepared tablet is sectioned in separate layers, each one comprising different active substances. One of the layers, preferably the innermost layer (core), comprises the acid-susceptible proton pump inhibitor in the form of coated pellets in admixture with pharmaceutical excipients and the other layer(s) comprise(s) the histamine H2-antagonist(s), respectively in admixture with pharmaceutical excipient(s). Optionally the two layers are separated by a separating layer to prevent tacking between the two layers. The coated core, comprising the acid-susceptible proton pump inhibitor may also advantageously be coated with an enteric layer by following, for instance, procedures disclosed in WO 00/78284, which is incorporated herein by reference.

According to the invention, the acid-susceptible proton pump inhibitor in the form of coated pellets may be mixed with histamine H2-antagonist(s) and optionally pharmaceutical excipient(s) to be administered in a sachet intended for oral administration after dispersion in a slightly acidic aqueous solution.

It is thus preferred for the dosage form of the invention to comprise the acid-susceptible proton pump inhibitor or a salt thereof protected by a coating layer for delayed and/or extended release and optionally also an enteric coating layer. Preferably the dosage form of the invention comprises two concentric layers optionally separated by one or more separating layer(s), one layer comprising said acid-susceptible proton pump inhibitor or salt thereof, the other layer comprising said H2 receptor antagonist or salt thereof.

The inner layer comprises the acid-susceptible proton pump inhibitor or a salt thereof and the outer layer comprises the H2 receptor antagonist or a salt thereof. According to a preferred aspect the outer layer comprises a disintegrant. The oral dosage form of the invention may take different shapes, such as a tablet, a capsule, a divided powder/pellet formulation, and the like.

Further, the proton pump-containing part of the formulations have above been described to exert their delayed and/or extended release effect by applying coatings to a core material of the proton pump inhibitor. However, another approach is instead to exchange the coating layer(s), i.e. the membrane system to a matrix system. The excipients are then chosen to form a lipid or water insoluble matrix. The function of the matrix is then to exert an extended release of the proton pump inhibitor.

According to the invention, there is also disclosed a method for the manufacture of an oral tableted dosage form comprising amounts of an acid-susceptible proton pump inhibitor or a salt thereof and an H2 receptor antagonist or a salt thereof pharmacologically effective in treating a condition related to dyspepsia, the method comprising forming a first layer comprising said acid-susceptible proton pump inhibitor or salt thereof, a coating of excipients for delayed and/or extended release and optionally an enteric coating surrounding said first layer, and a second layer comprising said H2 receptor antagonist or salt thereof surrounding said first layer and said coating. Also disclosed is a method for the manufacture of an oral dosage form comprising amounts of an acid-susceptible proton pump inhibitor or a salt thereof and an H2 receptor antagonist or a salt thereof pharmacologically effective in treating a condition related to dyspepsia, the method comprising forming pellets comprising said acid-susceptible proton pump inhibitor or salt thereof, covering said pellets with the above mentioned coatings, and mixing said pellets with a carrier comprising said H2 receptor antagonist or salt thereof; the carrier optionally comprising a disintegrant. The aforementioned methods of the invention further comprise a final tablet forming step, optionally followed by a film-covering step.

Another method for the manufacture of the oral dosage form of the invention comprises filling a capsule capable of disintegrating in gastrointestinal fluids to release its contents with the mixture comprising coated proton pump inhibitor pellets and a H2 receptor antagonist in powdery or granular form.

Regarding the methods for the manufacture, the proton pump-containing part of the formulations have above been described to exert their delayed and/or extended release effect by applying coatings to a core material of the proton pump inhibitor. However, another approach is instead to exchange the coating layer(s), i.e. the membrane system to a matrix system. The excipients are then chosen to form a lipid or water insoluble matrix. The function of the matrix is then to exert an extended release of the proton pump inhibitor.

The use of the pharmaceutical dosage form of the invention is however not restricted to provide quick and lasting relief to a patient suffering from conditions related to gastric acid secretion. The rapid onset of inhibition of gastric acid secretion combined with the maintenance of inhibition as long as desired (by repeated administration of a composition comprising an acid-susceptible proton pump inhibitor, preferably by repeated administration of the composition of the invention) can be expected to have a positive effect on the healing of gastric- and duodenal-ulcers and esophagitis for which the maintenance of intra-gastric pH above 4 for a maximal duration is acknowledged (Huang J Q and Hunt R H, pH, healing rate and symptom relief in patients with GERD, *Yale J Biol Med* 1999, 72:181-94). The composition of the invention thus is also preferred for maintaining gastric pH above 4 for extended periods of time, such as 4 hours and more.

The dosage form of the invention can also be used, in association with one or more antibiotic agent(s), for the eradication of *Helicobacter pylori*.

According to the invention, there is also disclosed a method of treating disorders associated with gastric acid secretion, the method comprising the administration of the dosage form of the invention or the concomitant administration of two separate oral dosage forms, one comprising a pharmacologically effective amount of an acid-susceptible proton pump inhibitor or a salt thereof, formulated for delayed and/or extended release, the other comprising a pharmacologically effective amount of an H2 receptor antagonist or a salt thereof, formulated for rapid release.

Furthermore, according to the invention, there is disclosed a method of treating an infection by *Helicobacter pylori*, comprising the administration of the dosage form of the invention or the concomitant administration of two separate oral dosage forms, one comprising a pharmacologically effective amount of an acid-susceptible proton inhibitor or a salt thereof, the other comprising a pharmacologically effective amount of an H2 receptor antagonist or a salt thereof, in association with the administration of one or more antibiotic agent(s) effective against *H. pylori*.

It is preferred for the aforementioned methods of treatment according to the invention to comprise a dose regimen capable of maintaining gastric pH above 4 for at least 95% of the time period starting at 2 hours from the administration of the first dose and extending until 6 hours from the administration of the last dose, in particular a regimen wherein the time period is one week or more, preferably two weeks or more, even more preferred four weeks or more. Also preferred in this context is a dose regimen capable of maintaining gastric pH above 3 for at least 95% of the time period starting at 2 hours from the administration of the first dose and extending until 6 hours from the administration of the last dose, in particular for four weeks or more.

The invention will now be described in greater detail by reference to a number of preferred but not limiting embodiments illustrated in a drawing.

BRIEF DESCRIPTION OF THE DRAWINGS

FIG. 1 a multiple unit tableted dosage form comprising an acid-susceptible proton pump inhibitor in the form of delayed and/or extended release coated pellets in admixture with an H2-receptor antagonist dispersed in a pharmaceutical carrier;

FIG. 2 a tableted dosage form consisting of two halves, one of which comprises delayed and/or extended release coating-covered pellets of an acid-susceptible proton pump inhibitor in admixture with excipients whereas the other comprises an H2 receptor antagonist in admixture with excipients;

FIG. 3 a multiple-layered tableted dosage form comprising an acid-susceptible proton pump inhibitor in a core surrounded by a delayed and/or extended release coating layer and a layer containing an H2 receptor antagonist dispersed in a pharmaceutical carrier surrounding the core;

FIG. 4 a capsule dosage form containing an acid-susceptible proton pump inhibitor in delayed and/or extended release coating-covered pellets in admixture with an H2 receptor antagonist and pharmaceutical excipients;

DESCRIPTION OF PREFERRED EMBODIMENTS

Figure 1:
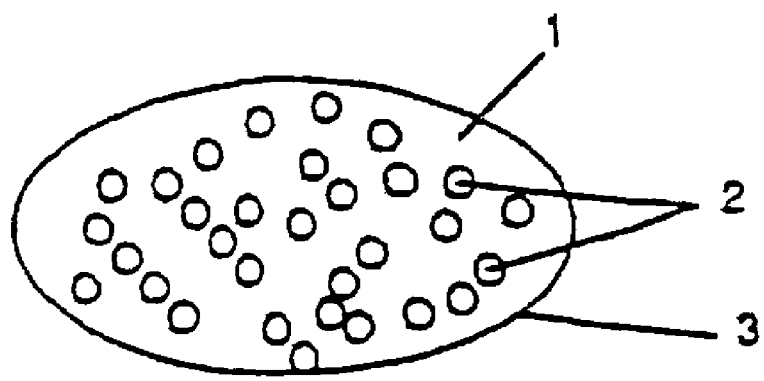
FIGS. 1-4 of the drawings are schematic cross sections illustrating.

Multiple-unit tableted dosage form: The multiple-unit tableted dosage form of the invention illustrated in FIG. 1 consists of a tablet body 1 optionally covered by a film layer 3 and small pellets 2 distributed at random in the tablet body 1. The pellets 2 contain an acid-susceptible proton pump inhibitor in form of the racemate, an alkaline salt or one of its enantiomers. The individual units 2 (small beads, granules or pellets) containing the acid-susceptible proton pump inhibitor and optionally containing alkaline substances, are coated with a layer(s) possessing delayed release and/or extended release and optionally an additional enteric coating layer. The coated units, 2 are then mixed with the H2 receptor antagonist and conventional tablet excipients forming, in combination, the tablet body 1. The H2 receptor antagonist and tablet excipients may be dry mixed or wet mixed into granules. The mixture of coated layered units, H2 receptor antagonist and excipients are compressed into the multiple unit tableted dosage forms. By the expression "individual units" is meant small beads, granules or pellets, in the following referred to as proton pump inhibitor pellets. In yet another embodiment of the invention, also the H2 receptor antagonist is coated onto the "individual units". Then the H2 receptor antagonist must be positioned in a peripheral position in relation to the coating layers for delayed and/or extended release and enteric release, in order to be rapidly released in the gastro-intestinal tract. In compressing the mixture into tablets, care must be taken not to significantly affect the acid resistance of the coated pellets. In regard of the core material for coating layered pellets comprising an acid-susceptible proton pump inhibitor reference is made to WO 97/25066, page 13, second to last paragraph, to page 15, end of second paragraph, which are hereby incorporated by reference. In regard of the coating layer(s) exerting the delayed and/or extended release reference is made to U.S. Pat. No. 6,274,173, which are hereby incorporated as reference. Reference is also made to "Pharmaceutics. The Science of Dosage Form Design.", 1$^{st}$ edition; Ed. M. E. Aulton, Churchill Livingstone, Edinburgh 1988. Reference is then especially made to pages 289-305. In regard of the enteric coating layer(s) reference is made to WO 97/25066, page 15, second to last paragraph, to page 18, end of second paragraph, which are hereby incorporated by reference. The acid-susceptible proton pump inhibitor pellets covered with layers for delayed and/or extended release and optionally an enteric coating layer(s) may be further covered with one or more over-coating layers. In regard of such over-coating layer(s) reference is made to WO 97/25066, page 18, last paragraph, to page 19, end of first paragraph, which are hereby incorporated by reference. The H2 receptor antagonist is dry mixed with inactive excipients such as filler, binders, disintegrants, and other pharmaceutically acceptable additives. The mixture is wet massed with a granulation liquid. The wet mass is dried preferably to a loss on drying of less than 3% by weight. Then the dry mass is milled to a suitable size for granules, preferably smaller than 1 mm. Suitable inactive excipients are, for instance, mannitol, corn starch, potato starch, low substituted hydroxypropyl cellulose, microcrystalline cellulose and crosslinked polyvinylpyrrolidone. The dry mixture comprising the H2 receptor antagonist may be mixed with a suitable granulation liquid comprising, for instance, hydroxypropylcellulose or polyvinyl-pyrrolidone dissolved in water or alcohol or their mixtures. Alternatively the H2 receptor antagonist is dry mixed with pharmaceutically acceptable excipients (see supra). As mentioned above, in another embodiment of the invention the H2 receptor antagonist can be coated onto the small units, 2, rather than mixed with excipients to form the tablet body, 1. Irrespective of how the H2 receptor antagonist is incorporated it should possess a rapid release.

Multi-unit tablets: The coated layered pellets comprising an acid-susceptible proton pump inhibitor are mixed with the H2 receptor antagonist granules or with the prepared dry mixture comprising the H2 receptor antagonist. The mixture is admixed with lubricant(s) and compressed into a multiple unit tableted dosage form. Suitable lubricants for the tableting process are, for instance, sodium stearyl fumarate, magnesium stearate and talc. The compressed tablets are optionally covered with film-forming agent(s) to obtain a smooth surface. Such a coating layer may further comprise additives such as anti-tacking agents, colorants and pigments or other additives.

The fraction of coated pellets preferably constitutes less than 60% by weight of the total tablet weight. The preferred multiple-unit table formulation thus consists of delayed and/or extended release coated layered pellets optionally coated with an enteric coating layer, comprising the acid-susceptible proton pump inhibitor, optionally in admixture with alkaline reacting compound(s), compressed into tablets with the prepared H2 receptor antagonist/excipient(s) mixture. The optional enteric coating layer(s) make(s) the pellets of the dosage form insoluble in acidic media but disintegrating/dissolving in near neutral to alkaline media, such as the gastric fluid present in the proximal part of the small intestine where the dissolution and uptake of the acid-susceptible proton pump inhibitor is desired. The delayed release coating layer, will then start to release the acid susceptible proton pump inhibitor after a certain time period in the gastrointestinal tract or at a certain pH, reached at some position in the intestine or colon. The extended release coating layer will extend the release of the proton pump inhibitor in order to result in drug absorption during several hours. The delayed and/or extended release coated proton pump inhibitor pellets may also be covered with an overcoating layer before being formulated into tablets, and they may also contain one or more separating layer(s) in between the core material and the other layers.

Process for making multi-unit tablets: The process for the manufacture of this dosage form represents a further aspect of the invention. After formulating the pellets by dry mixing (ordered mixture), spray coating or layering of the acid-susceptible proton pump inhibitor onto seeds, or by extrusion/spheronization or granulation, the pellets are first optionally covered with the separating layer(s) and then covered with the delayed and/or extended release layer(s) and then optionally covered with the enteric coating layer(s). The coating is carried out as described above and in the accompanying examples. The preparation of the H2 receptor antagonist mixture is also described in the examples. Optionally the H2 receptor antagonist can be coated onto the already existing layers comprising delayed and/or extended release layer(s) and enteric coating layer.

Figure 2:
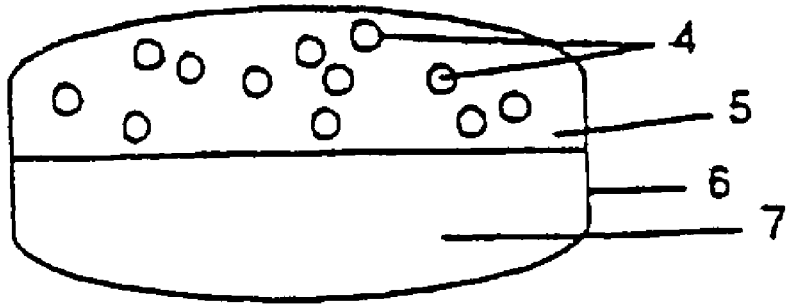
Figure 3:
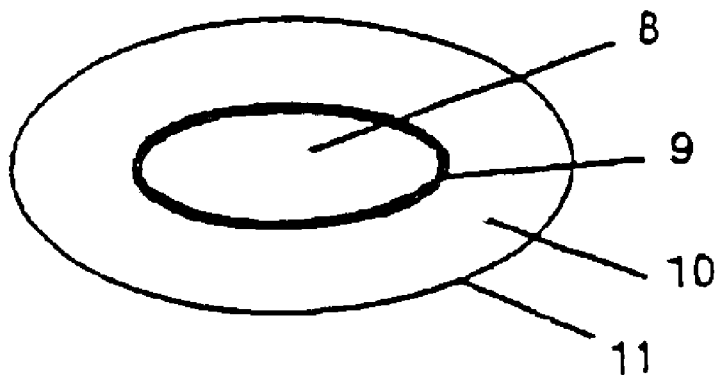

The coated pellets, with or without an overcoat, are mixed with the prepared H2 receptor antagonist granules or dry powder, tablet excipients and other pharmaceutically acceptable additives and compressed into tablets. Alternatively, the coated proton pump inhibitor pellets may be covered by a second layer containing the H2 receptor antagonist as described in the following examples. Furthermore, as illustrated in FIG. 2, the coated pellets 4 may be intimately mixed with excipients 5 and pre-compressed whereafter the H2 receptor antagonist preparation 7 is added and the entire tablet mass finally compressed into a tablet, optionally with film-forming agent(s) 6 to obtain a smooth surface. As a further alternative illustrated in FIG. 3, the acid-susceptible proton pump inhibitor in the form of a powder may be mixed with tablet excipients and compressed into a tablet 8 which is optionally covered with a separating layer and thereafter covered with delayed and/or extended release coating 9. Optionally, an enteric coating layer is applied. The thus produced tablet core is subsequently press-coated with the H2 receptor antagonist preparation 10. Finally the table may be covered with a tablet coat 11 to obtain a smooth surface.

It is also possible to fill the acid-susceptible proton pump inhibitor in form of coated layered pellets in a sachet together with H2 receptor antagonist and optionally mixed with excipients.

Figure 4:
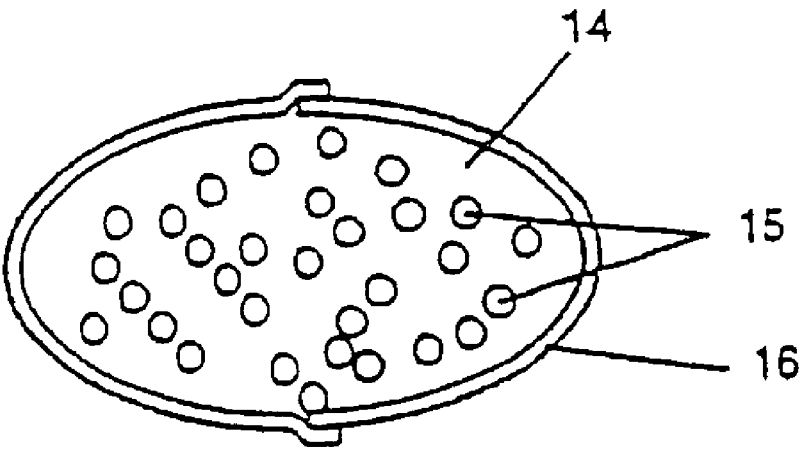

FIG. 4 illustrates a hard gelatin capsule 16 filled with the uncompressed core material 14, 15 of the embodiment of FIG. 1.

In the examples given (FIGS. 1, 2, 3 and 4) the terms coating, coating layer or layer have been used. These terms are exchangeable and also identical to the term membrane. Irrespective of the nomenclature they have in common that they correspond to more or less continuous phases of excipient materials applied by e.g. spraying onto a core material. Due to the nature of the processing these membranes are relatively thin with regard to thickness.

Suitable excipient materials for forming coatings layers (or membranes) for delayed and/or extended release are non-polymeric—or polymeric materials such as calcium phosphate, ethyl cellulose, methacrylate copolymer, polyamide, polyethylene, polyvinyl alcohol or polyvinyl acetate.

Further, the proton pump-containing part of the formulations (2 in FIG. 1, 4 in FIG. 2, 8 in FIG. 3 and 15 in FIG. 4) have above been described to exert their delayed and/or extended release effect by applying coatings to a core material of the proton pump inhibitor. However, another approach is instead to exchange the coating layer(s), i.e. the membrane system to a matrix system. The excipients are then chosen to form a lipid or water insoluble matrix. The function of the matrix is then to exert an extended release of the proton pump inhibitor. Suitable matrix forming excipients are non-polymeric—or polymeric materials such as calcium phosphate, ethyl cellulose, methacrylate copolymer, polyamide, polyethylene or polyvinyl acetate, carnauba wax, cetyl alcohol, hydrogenated vegetable oils, microcrystalline waxes, mono- and triglycerides, polyethylene glycol or polyethylene glycol monostearate and most preferably carnauba wax, cetyl alcohol, hydrogenated vegetable oils, microcrystalline waxes, mono- and triglycerides, polyethylene glycol or polyethylene glycol monostearate. In order to obtain an optimal release rate, hydrophilic, pore-forming excipients can be optionally added. Suitable hydrophilic, pore forming materials are alginates, carbopol, gelatin, hydroxypropyl cellulose, hydroxypropyl metylcellulose or metylcellulose.

In general, the methods of WO 97/25066 for making oral pharmaceutical dosage forms comprising an acid susceptible proton pump inhibitor and an antacid agent or alginate can be adapted to suit the purpose of the present invention by firstly, adding the membrane—or matrix system to the part of the formulation that contains the proton pump inhibitor and secondly, by substituting part or the entire amount of antacid agent or alginate by a pharmacologically effective amount of an H2 receptor antagonist, the remainder of the antacid agent or alginate (if substitution is not 1:1 by weight) being omitted or substituted by excipients like microcrystalline cellulose, silica, lactose, mannitol, ant the like.

Use of the Dosage Forms According to the Invention.

The dosage forms according to the invention are especially advantageous in the treatment of dyspepsia and other gastrointestinal disorders related to the production of gastric acid to provide quick and lasting relief from symptoms. The dosage forms are administered once or several times a day. The typical daily dose of the acid-susceptible proton pump inhibitor and the H2 receptor antagonist will depend on various factors such as individual requirements of patients, the mode of administration, and the particular condition to be treated. In general each dosage form will comprise from 1 mg to 100 mg of acid-susceptible proton pump inhibitor and from 1 to 800 mg of the H2 receptor antagonist. Preferably each dosage form will comprise from 5 to 50 mg of the acid-susceptible proton pump inhibitor and from 5 to 200 mg of the H2 receptor antagonist. The multiple unit tablet preparation is also suitable for dispersion in water, which has been made slightly acidic by the addition of citric acid.

Example 1

Multiple-unit tableted dosage form comprising magnesium omeprazole and cimetidine hydrochloride; batch size 400 tablets. For omeprazole Mg-salt pellet production (core material, separating layer, enteric coating layer and overcoating layer, see WO 97/25066, p. 22-23 under respective headings), see WO 97/25066, first two paragraphs, all of which is hereby incorporated by reference. The extended release layer is applied, by a coating process, in between the separation layer and the enteric coating layer, in accordance with what is described in patent U.S. Pat. No. 6,274,173, Example 1-4, using ethyl cellulose or polyvinyl acetate as extended release forming excipients, the information under which is hereby incorporated as reference.

| Tablets | |
|---|---|
| Prepared pellets comprising omeprazole Mg-salt | 31.3 g |
| Microcrystalline cellulose | 300.0 g |
| Cimetidine hydrochloride | 40.0 g |
| Potato starch | 50.0 g |
| Water | 200.0 g |
| PVP crosslinked | 38.0 g |
| Sodium stearyl fumarate | 4.6 g |

A small amount of the potato starch is dissolved in purified hot water to form the granulation liquid. Cimetidine hydrochloride, the rest of potato starch and microcrystalline cellulose are dry mixed. The granulation liquid is added to the dry mixture and the mass is wet mixed. The wet mass is dried in an oven at 50° C. The prepared granulation is milled through sieve 1 mm in an oscillating mill equipment. The coated pellets with an over-coating layer, the prepared H2 receptor antagonist granules, cross-linked polyvinylpyrrolidone and sodium stearyl fumarate are mixed and compressed into tablets using a tableting machine equipped with oval punches. The amount of omeprazole in each tablet is approx. 10 mg and the amount of cimetidine hydrochloride is approx. 100 mg.

By a slight modification this multiple-unit tablet form can be made to comprise an antacid agent (instead of microcrystalline cellulose, 300 mg: microcrystalline cellulose, 100 g; calcium carbonate, 100 mg; magnesium oxide, 100 mg; all other constituents, except water, in the amounts given above).

Example 2

Three-Layered Tableted Dosage Form

The tablet comprises the acid-susceptible proton pump inhibitor omeprazole, a separating layer and a core layer comprising cimetidine hydrochloride. Batch size 1000 tablets.

| First tablet layer | |
|---|---|
| Cimetidine hydrochloride | 200.0 g |
| Microcrystalline cellulose | 250.0 g |
| PVP crosslinked | 13.0 g |
| Sodium stearyl fumarate | 3.8 g |

| Separating layer | |
|---|---|
| Microcrystalline cellulose | 80.0 g |

| Second tablet layer | |
|---|---|
| Coated pellets comprising omeprazole magnesium salt (same as in EXAMPLE 1) | 78.3 g |

| -continued | |
|---|---|
| Second tablet layer | |
| Microcrystalline cellulose | 174.0 g |
| PVP crosslinked | 26.0 g |
| Sodium stearyl fumarate | 1.4 g |

The constituents of the first tablet layer are dry mixed and pre-compressed as a first layer in a tableting machine equipped with oval punches. Microcrystalline cellulose is filled on the top of the first layer to form a separating layer to the next layer. The constituents of the second tablet layer are dry mixed and filled on top of the separating layer. The three layers are compressed into a three-layer tablet, which may be coated by a tablet coating layer. The amount of omeprazole is approx. 10 mg and that of cimetidine hydrochloride approx. 200 mg per tablet.

Example 3

Capsule Dosage Form

No. 1 hard gelatin capsules (16) (FIG. 4; volume 0.48 ml) were filled with extended release-coated omeprazole pellets (15) containing 20 mg omeprazole (as prepared in EXAMPLE 1) and a dry mixture 14 of commercially available famotidine 20 mg and closed.

Example 4

Divided Powder/Pellet Formulation

Extended release pellets containing 15 mg lansoprazole (as prepared in analogy with EXAMPLE 1) and the famotidine preparation were dry mixed with citric acid. Single dose portions thereof containing 10 mg each of lansoprazole and famotidine hydrochloride and 200 mg powderous citric acid were dry packed in plastic laminate. The composition is intended to be poured into 20 ml of water, stirred for a short time, and swallowed.

Example 5

Multiple-Unit Capsule Dosage Form

The capsule comprises magnesium omeprazole and famotidine hydrochloride. For extended release coating layer, see U.S. Pat. No. 6,274,173, Example 1-4, the information under which is hereby incorporated as reference. For enteric coating layer and over-coating layer, see WO 97/25066, page 22-23 under respective headings, the information under which is hereby incorporated by reference.

Magnesium omeprazole is mixed with microcrystalline cellulose spheres to an ordered mixture. The ordered mixture is coated with an extended release layer, consisting of polyvinyl acetate, micronised lactose, propylene glycol and ammonia (25%) in a fluid bed apparatus. These extended release pellets were the coated with an enteric coating layer consisting of methacrylic acid copolymer, mono- and diglycerides, triethyl citrate and polysorbate in a fluid bed apparatus. The extended release/enteric coated ordered units is then over-coated with a water suspension containing famotidine hydrochloride, hydroxypropylmethyl cellulose and magnesium stearate in a fluid bed apparatus. The extended release/ enteric coated ordered mixture with an over-coating layer was filled into hard gelatin capsules. The amount of omeprazole is approx. 10 mg and that of famotidine hydrochloride approx. 20 mg per capsule.

Example 6

Multiple-Unit Tableted Dosage Form

The tablet comprises magnesium omeprazole and cimetidine hydrochloride. Magnesium omeprazole is mixed with mannitol granules to an ordered mixture which is coated with both an extended release coating layer and an enteric coating layer as described in EXAMPLE 5. Cimetidine hydrochloride is granulated as described in EXAMPLE 1. The coated ordered mixture comprising magnesium omeprazole, the cimetidine granules and excipients are dry mixed and compressed into tablets. The amount of omeprazole in each tablet is approx. 10 mg and that of cimetidine is approx. 100 mg.

Example 7

Multiple-unit tableted dosage form for instant release of H2 receptor antagonist and colon extended release of proton pump inhibitor. The tablet comprises magnesium omeprazole and cimetidine hydrochloride.

| Core material | |
|---|---|
| Omeprazole magnesium salt | 120 g |
| Sugar sphere seeds | 150 g |
| Hydroxypropyl methylcellulose | 18 g |
| Polysorbate 80 | 2.4 g |
| Water purified | 562 g |

Suspension layering was performed in a fluid bed apparatus. Omeprazole magnesium salt was sprayed onto sugar sphere seeds from a water suspension containing the dissolved binder and polysorbate 80. The size of sugar sphere seeds were in the range of 0.25 to 0.35 mm.

| Extended release layer | |
|---|---|
| Core material (acc. to above) | 200 g |
| Eudragit ® RTM | 100 g |
| Hydroxypropyl cellulose | 10 g |

| Delayed release layer | |
|---|---|
| Pellets covered with extended release layer (acc. to above) | 250 g |
| Eudragit ® FS 30 D | 100 g |

The prepared core material was covered with both an extended release layer and a delayed release layer in a fluid bed apparatus with commercially available water-based suspensions, Eudragit® RTM and Eudragit® FS 30 D, respectively.

| Enteric coating layer | |
|---|---|
| Pellets covered with both a delayed release and extended release layer (acc. to above) | 250 g |
| Methacrylic acid copolymer (30% suspension) | 333.7 g |
| Triethyl citrate | 30 g |
| Mono- and diglycerides (NF) | 5 g |
| Polysorbate 80 | 0.5 g |
| Water purified | 196 g |

The enteric coating layer consisting of methacrylic acid copolymer, mono- and diglycerides, triethyl citrate and polysorbate was sprayed onto the pellets covered with extended/delayed release layers in a fluid bed apparatus. The enteric coating layered pellets were classified by sieving.

| Tablets | |
|---|---|
| Prepared pellets comprising omeprazole Mg-salt | 63.7 g |
| Cimetidine hydrochloride | 65.0 g |
| Calcium carbonate | 123.9 g |
| Magnesium hydroxide | 123.9 g |
| Potato starch | 52.2 g |
| Water purified | 435 g |
| Microcrystalline cellulose | 175 g |
| Polyvidone crosslinked | 50.0 g |
| Sodium stearyl fumarate | 6.0 g |

A small amount of the potato starch was dissolved in hot purified water to form the granulation liquid. Cimetidine hydrochloride, calcium carbonate, magnesium hydroxide and potato starch were dry-mixed. The granulation liquid was added to the dry mixture and the mass was wet-mixed.

The wet mass was dried in a steamoven at 40 DEG C. The prepared granulation was milled through sieve 1 mm in an oscillating mill equipment.

The multiple coated layered pellets, prepared granules, polyvidone crosslinked, microcrystalline cellulose and sodium stearyl fumarate were mixed and compressed into tablets using a tableting machine equipped with 9.times.20 mm oval punches. The amount of omeprazole in each tablet was approx. 20 mg and the same amount was used for cimetidine hydrochloride.

Tablet hardness was measured to 30N.

Optionally the obtained tablets were covered with a tablet coating layer.

The invention claimed is:

1. A method for treating at least one symptom of gastro-esophageal reflux disease (GERD) in a human suffering from GERD consisting essentially of
   (i) providing an oral dosage form for release of active ingredients in a gastro-intestinal tract consisting essentially of a proton pump inhibitor (PPI) selected from a group consisting of lansoprazole, omeprazole, pantoprazole, rabeprazole, pariprazole, leminoprazole, and their pharmaceutically acceptable salts, isomers including enantiomers, and pharmaceutically acceptable salts of said isomers, an H2 receptor antagonist selected from a group consisting of cimetidine, ranitidine, nizatidine and famotidine, and their pharmaceutically acceptable salts, isomers, and pharmaceutically acceptable salts of said isomers, and a coating on the PPI and not on the H2RA to delay and/or extend the release of the PPI relative to the release of the H2RA in the gastro-intestinal tract, and ooptionally an antacid agent or an alginate,
   (ii) adopting a dose regime for the oral dosage form by selecting a dosage amount of the PPI with the coating and a dosage amount of the H2RA free of a coating to affect, upon simultaneous administration to the gastro-intestinal tract, a rise in gastric pH to above about 3 within about 2 hours of administration,
(iii) orally administering the oral dosage form according to the dose regime to deliver into the gastro-intestinal tract the selected dosage amount of the PPI including the coating simultaneously with the selected dosage amount of the H2RA free of a coating and affect a rise in gastric pH to above about 3 within about 2 hours of the oral dosage, thereby treating the at least one symptom of GERD promptly, and
(iv) repeating (iii) if necessary over a prolonged period until 6 hours from the administration of the last dose
wherein the at least one symptom of GERD is selected from a group consisting of heartburn, sour stomach, and upper abdominal pain.

2. A method as claimed in claim 1, wherein the dosage form contains the antacid agent or the alginate.

3. A method as claimed in claim 2, wherein the antacid agent comprises at least one of aluminum hydroxide, calcium carbonate, magnesium carbonate, basic magnesium carbonate, magnesium hydroxide, magnesium oxide and/or sodium hydrogen carbonate.

4. A method according to claim 1, wherein the oral dosage form includes a core comprising the PPI, and wherein the coating comprises a membrane applied onto the core.

5. A method according to claim 4, wherein the H2RA forms an outer layer applied onto the membrane of the core.

6. A method according to claim 1, wherein the PPI and the coating are incorporated into a matrix.

7. A method according to claim 6, wherein the H2RA forms an outer layer applied onto the matrix.

8. A method according to claim 4, wherein the membrane comprises non-polymeric or polymeric materials including calcium phosphate, ethyl cellulose, methacrylate copolymer, polyamide, polyethylene, polyvinyl alcohol or polyvinyl acetate.

9. A method according to claim 6, wherein the matrix comprises non-polymeric or polymeric materials including calcium phosphate, ethyl cellulose, methacrylate copolymer, polyamide, polyethylene, polyvinyl alcohol or polyvinyl acetate.

10. A method according to claim 4 or 5, wherein the oral dosage form includes an enteric coating layer applied onto the membrane.

11. A method according to claim 10, wherein the oral dosage form includes a layer separating the enteric coating layer from the membrane.

12. A method according to claim 6, wherein the oral dosage form includes an enteric coating layer applied onto the matrix.

13. A method according to claim 12, wherein the oral dosage form includes a layer separating the enteric coating layer from the matrix.

14. A method according to claim 4, or 5, or 6, or 7, wherein the oral dosage form includes an alkaline-reacting substance admixed together with the PPI.

15. A method according to claim 1, wherein the oral dosage form is presented as a tablet or capsule within which the PPI and the coating are presented as a plurality of small dosage units comprising pellets, granules or beads distributed within the tablet or capsule.

16. A method according to claim 15, wherein the tablet or capsule further comprises a H2RA.

17. A method according to claim 15 or 16, wherein the tablet or capsule further comprises a pharmaceutically acceptable excipient.

18. A method according to claim 17, wherein the pharmaceutically acceptable excipient comprises a disintegrant.

19. A method according to claim 5 or 7, wherein the dosage form is presented in two halves.

20. A method according to claim 19, wherein the dosage form further includes a pharmaceutically acceptable excipient.

21. A method according to claim 20, wherein the pharmaceutically acceptable excipient comprises a disintegrant.

* * * * *